(12) United States Patent
Pettovello

(10) Patent No.: US 6,449,621 B1
(45) Date of Patent: Sep. 10, 2002

(54) PRIVACY DATA ESCROW SYSTEM AND METHOD

(75) Inventor: Primo Mark Pettovello, Canton, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/433,806

(22) Filed: Nov. 3, 1999

(51) Int. Cl.[7] .............................. G06F 17/00; G06F 7/00

(52) U.S. Cl. ........................ 707/104.1; 705/2; 713/200; 707/10

(58) Field of Search ........................... 707/9–10, 104.1; 713/200–202; 705/2–3

(56) References Cited

U.S. PATENT DOCUMENTS

| | | | | |
|---|---|---|---|---|
| 5,325,294 A | * | 6/1994 | Keene | 705/3 |
| 5,499,293 A | | 3/1996 | Behram et al. | 705/76 |
| 5,579,393 A | | 11/1996 | Conner et al. | 713/176 |
| 5,606,610 A | * | 2/1997 | Johansson | 713/193 |
| 5,832,488 A | | 11/1998 | Eberhardt | 707/10 |
| 5,956,400 A | | 9/1999 | Chaum et al. | 713/167 |
| 6,023,721 A | * | 2/2000 | Cummings | 709/201 |
| 6,148,342 A | * | 11/2000 | Ho | 709/225 |
| 6,205,472 B1 | * | 3/2001 | Gilmour | 709/206 |
| 6,253,203 B1 | * | 6/2001 | O'Flaherty et al. | 707/9 |
| 6,275,824 B1 | * | 8/2001 | O'Flaherty et al. | 707/9 |
| 2002/0029156 A1 | * | 3/2002 | O'Dowd | 705/3 |

FOREIGN PATENT DOCUMENTS

| | | | | |
|---|---|---|---|---|
| EP | 0 884 670 A1 | 2/1998 | | |
| EP | 0 950 972 A2 | 10/1999 | | |
| EP | 1099996 A1 | * | 5/2001 | G06F/1/00 |
| WO | WO 95/15628 | * | 6/1995 | H04K/1/00 |
| WO | WO 99 38080 | 1/1998 | | |

OTHER PUBLICATIONS

JHMI–Infonet, "JHBMC–IRB Guidelines: Data Safety Monitoring Evaluation", Nov. 1997, downloaded from infonet.welch.jhu.edu/research/jhbmc-irb/guide-C-6.html, on Nov. 2, 2001.*

Department of Health and Human Services, National Institutes of Health, "Privacy Act of 1974; New System of Records", Apr. 4, 1997, downloaded from www.nimh.nih-.gov/grants/privacyact1997.pdf on Nov. 2, 2001.*

U.S. Congress, Office of Technology Assessment, "Protecting Privacy in Computerized Information, OTA–TCT–576" (Washington, DC:U.S. Government Printing Office, Sep. 1993.*

(List continued on next page.)

Primary Examiner—Jean R. Homere
Assistant Examiner—Luke S Wassum
(74) Attorney, Agent, or Firm—Baker Botts L.L.P.

(57) ABSTRACT

The privacy data escrow system (10) includes at least one data provider (12) having a plurality of privacy data records of a plurality of persons. Each privacy data record is associated with a unique person identifier of a person, and each of the at least one data provider (12) having a unique data provider identifier associated therewith. An escrow agent (16) is in communication with the at least one data provider (12) and is operable to receive and store, from the at least one data provider (12), the plurality of person identifiers, and a plurality of unique scrambled person identifiers and data provider identifiers associated with each person identifier (14). A database (20) is in communication with the at least one data provider (12) and is operable to receive and store, from the at least one data provider (12), the plurality of privacy data records, the plurality of scrambled person identifiers associated with the privacy data records, and the data provider identifiers (13). The database (20) is further operable to receive and store, from the escrow agent (16), a unique universal anonymous identifier to replace each scrambled person identifier (18) whereby each privacy data record stored in database is identifiable by a universal anonymous identifier.

19 Claims, 1 Drawing Sheet

OTHER PUBLICATIONS

Federal Register of Tuesday, Jun. 18, 1991, "Part II: Federal Policy for the Protection of Human Subjects; Notices and Rules", vol. 56, No. 117, pp. 28002–28032.*

Federal Register of Monday Jun. 19, 1989, "Privacy Act of 1974; Final Guidance Interpreting the Provisions of Public Law 100–503, the Computer Matching Privacy Protection Act of 1988", vol. 54, No. 116, pp. 25818–25829.*

National Research Council, "For The Record: Protecting Electronic Health Information", Washington, DC:National Academy Press, 1997, pp. 1–18 and 82–135, R864,F67 1997.*

National Research Council, "Cryptography's Role in Securing the Information Society", Washington, DC:National Academy Press, 1996, pp. 457–461 TK5102.94.C78 1996.*

Coleman, M.P., Muir, C.S. and Menegoz, F. "Confidentiality in the Cancer Registry", British Journal of Cancer, vol. 66, No. 6, Dec. 1992, pp. 1138–1149.*

Bharucha–Reid, R.P., Schork, M.A. and Schwartz, S.A. "Data Linkage and Subject Anonymity for HIV Testing", AIDS Public Policy Journal, vol. 5, No. 4, Winter 1990, pp. 189–190.*

Abi Berger, Private Company Wins Right To Icelandic Gene Database (BMJ 1999; 318:11 (Jan. 2)) (visited Aug. 16, 1999 @3:05 p.m.) <http://www/bmj.com/cgi/content/short/318/7175/11>.

John Schwartz, Iceland Sells Its People's Genetic Code To Biotech Firm (The Washington Post, Posted at 08:45 a.m. PST; Tuesday, Jan. 12, 1999) (visited Aug. 16, 1999 @3:10 p.m.) <http://www.seattletimes.com/news/nations–world/html98/altgene_011299.html>.

No names or personal IDs enter DeCODE genetics (visited Aug. 16, 1999 @ 3:15 p.m.) <http://www.decode.is/ppt/protection/sld003.htm>.

* cited by examiner

PRIVACY DATA ESCROW SYSTEM AND METHOD

TECHNICAL FIELD OF THE INVENTION

This invention is related in general to the field of computers and computer databases, and more particularly, to a privacy data escrow system and method.

BACKGROUND OF THE INVENTION

In today's computer age, nearly every human action leads to the generation, collection and storage of some data. For example, a shopper's grocery or merchandise purchasing habits are collected at the checkout line and stored in databases for future marketing or customer relation purposes. In some instances, sensitive personal data collection leads to privacy issues. For example, financial data are collected whenever a customer applies for credit or a loan, and medical records are maintained for patients for insurance claim purposes. In the latter example, special concerns exist for employees whose employers maintain health care records of its employees. The challenge for employers is to maintain the confidentiality and privacy of employee health medical and claims data, while permitting access to the data for research, analysis, and, in some cases, targeted patient intervention.

SUMMARY OF THE INVENTION

It has been recognized that it is desirable to provide a privacy data escrow system and method to maintain the confidentiality of sensitive personal data such as patient medical records.

In one aspect of the invention, a privacy data escrow system includes at least one data provider having a plurality of privacy data records of a plurality of persons. Each privacy data record is associated with a unique person identifier of a person, and each of the at least one data provider having a unique data provider identifier associated therewith. An escrow agent is in communication with the at least one data provider and is operable to receive and store, from the at least one data provider, the plurality of person identifiers, and a plurality of unique scrambled person identifiers and data provider identifiers associated with each person identifier. A database is in communication with the at least one data provider and is operable to receive and store, from the at least one data provider, the plurality of privacy data records, the plurality of scrambled person identifiers associated with the privacy data records, and the data provider identifiers. The database is further operable to receive and store, from the escrow agent, a unique universal anonymous identifier to replace each scrambled person identifier whereby each privacy data record stored in database is identifiable by a universal anonymous identifier.

In another aspect of the invention, a privacy data escrow system includes at least one data provider having a plurality of privacy data records of a plurality of persons, each privacy data record being associated with a unique person identifier of a person, each of the at least one data provider having a unique data provider identifier associated therewith, the at least one data provider being operable to scramble the person identifiers and generate unique scrambled person identifiers therefrom. An escrow agent is in communication with the at least one data provider and is operable to receive and store, from the at least one data provider, the plurality of person identifiers, the associated scrambled person identifiers, and the associated data provider identifier, the escrow agent being operable to generate a unique universal anonymous identifier for each scrambled person identifier. A database in communications with the at least one data provider and is operable to receive and store, from the at least one data provider, the plurality of privacy data records, the plurality of scrambled person identifiers associated with the privacy data records, and the data provider identifier. The database is further operable to receive and store, from the escrow agent, a unique universal anonymous identifier to replace each scrambled person identifier whereby each privacy data record stored in database is identifiable by a universal anonymous identifier.

In yet another aspect of the invention, a method of maintaining the confidentiality of privacy data includes the steps of associating a unique person identifier with each privacy data record, scrambling the unique person identifier and generating a scrambled person identifier, transmitting the privacy data record and the scrambled person identifier to a database for storage, and transmitting the person identifier with its associated scrambled person identifier to an escrow agency for confidential safekeeping. The escrow agency then generates a universal anonymous identifier for each person identifier and scrambled person identifier, and transmits the universal anonymous identifier and its associated scrambled person identifier to the database.

BRIEF DESCRIPTION OF THE DRAWINGS

For a better understanding of the present invention, reference may be made to the accompanying drawings, in which.

DETAILED DESCRIPTION OF THE INVENTION

Figure 1:
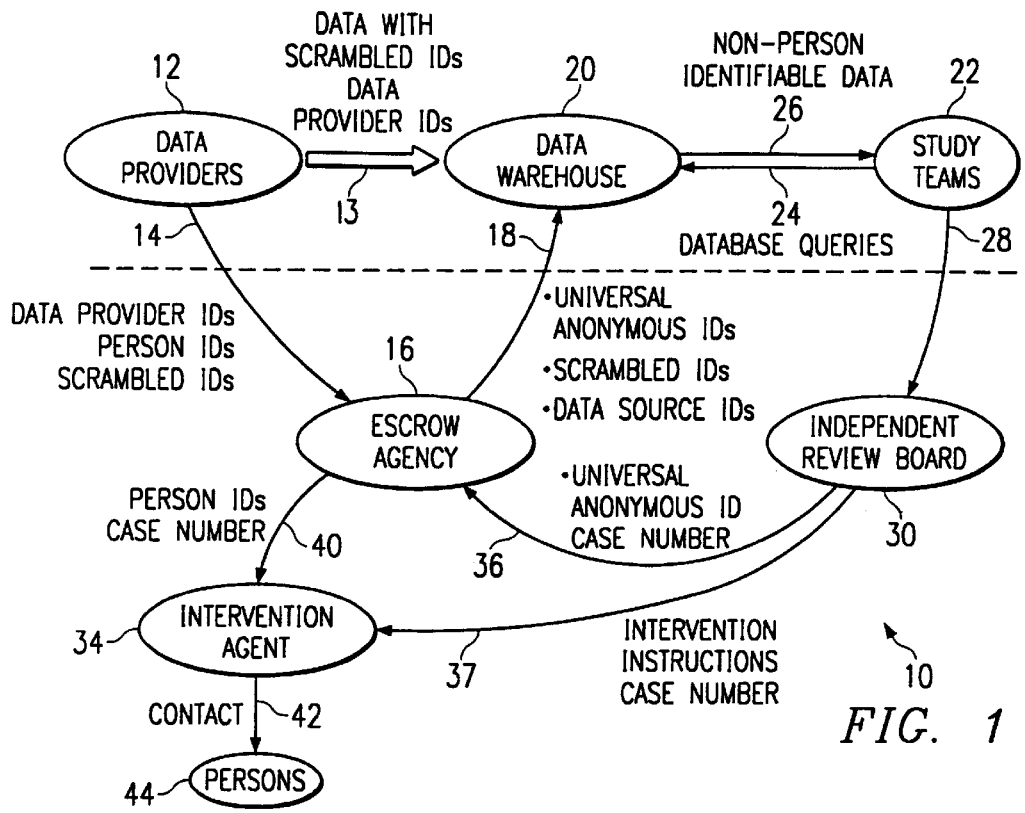
FIG. 1 is a simplified data flow diagram of an embodiment of the privacy data escrow system and method according to the teachings of the present invention.

FIG. 1 is a simplified data flow diagram of an embodiment of the privacy data escrow system and method 10 according to the teachings of the present invention. Privacy data escrow system 10 obtains sensitive or confidential data from one or more sources or data providers 12. Data providers 12 may be persons, entities, organizations, or companies that have possession of the sensitive data. A data provider 12 may or may not have collected the data itself. In the patient medical records example described above, data providers 12 may be employee health insurance carriers, and the medical records typically include a person identifier such as the social security number of the patient. The medical records may further contain other person identifiable attributes such as name, work and home addresses, work and home phone numbers, and like information. The sensitive data may be insurance claims, clinical records, pharmacy records, occupational health information, worker's compensation information, financial information, personnel information and other data. However, sensitive and confidential data of another nature may be protected by system 10 in the same manner.

Prior to releasing the sensitive data, data provider 12 separates the person identifier from the rest of the data and scrambles the person identifier. Any data scrambling, encoding or encryption algorithm may be used. The scrambling algorithm may even be a random number generator which uses the person identifier as the seed number. Data provider 12 then transmits or sends a data feed of the data with the scrambled person identifier and a data provider identifier (13) to a database, data management system, or data warehouse 20 for data storage. The sensitive data stored in database 20 is therefore associated only with a data provider identifier and a scrambled person identifier. Data provider 12 also transmits the scrambled person identifier and the associated person identifier along with the data provider identifier (14) to a trusted escrow agent 16 for safe keeping. Other person identifiable attributes which may be used to identify the person are also transmitted to escrow agent 16. Escrow agent 16 therefore possesses a mapping of the scrambled person identifier to the person identifier and other person identifiable attributes. The mapping information may be represented in the form of a table.

Escrow agent 16 then generates a unique universal anonymous identifier for each person identifier. This universal anonymous identifier is transmitted along with the associated scrambled person identifier and data provider identifier to a database 20. Database 20 thus has sufficient information to map or otherwise associate the scrambled person identifiers to the corresponding universal anonymous identifiers, but not to the person identifiers. In fact, database 20 does not possess any data on the person identifiers or any other data attributes that can be used to identify the person. The universal anonymous identifier is used to reference all data related to a specific person regardless of the identity of the data source or data provider 12. Therefore, each person may be referenced by a unique universal anonymous identifier in database 20 without compromising the confidentiality of the data.

Figure 2:
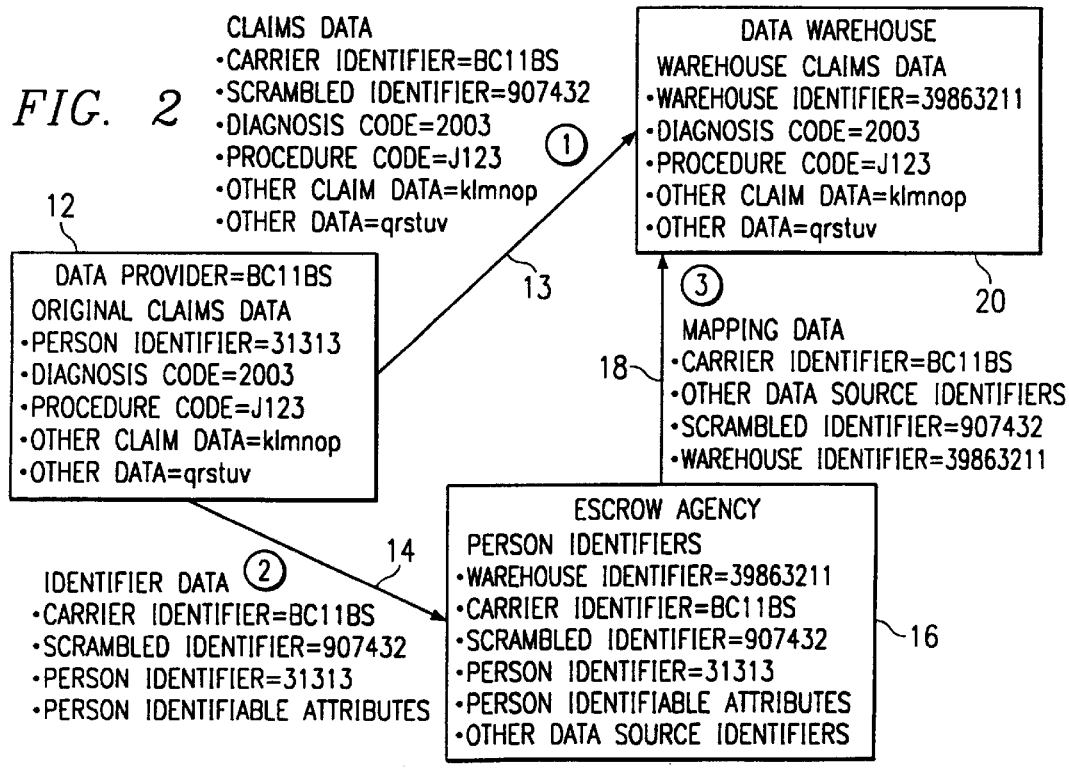
FIG. 2 is a more detailed numerical data flow example of an embodiment of the process of separating and scrambling person identifiers from the data according to the teachings of the present invention.

FIG. 2 is a more detailed numerical data flow example of an embodiment of the process of separating and scrambling person identifiers from the data according to the teachings of the present invention. The data shown are merely for demonstration purposes and do not resemble actual data.

Data provider 12 may be a health insurance carrier, which has an identifier of "BC11BS," for example. Each data provider 12 in system 10 is uniquely identifiable by a data provider identifier. Data provider 12 has a set of original claims data related to a person identified by person identifier "31313," for example. Typically, the original claims data also includes other person identifiable attributes, such as name, address, phone number, etc. The original claims data in possession by data provider 12 may also include a diagnosis code ("2003"), a procedure code ("J123"), other claims data ("klmnop"), and other assorted data ("qrstuv"). Data provider 12 then applies a scrambling algorithm to methodically alter the person identifier, so that it is now "907432". The scrambled person identifier is unique to each person identifier or person. The scrambled person identifier is transmitted or fed to database 20 with the data provider identifier and the remaining data (for example, diagnosis code, procedure code, other claims data, and other data). Only the person identifier is scrambled or altered from the original. The data is typically transmitted electronically to database 20 via a data feed or EDI (electronic data interchange).

Data provider 12 also transmits to escrow agent 16 the same scrambled person identifier ("907432"), the data provider identifier ("BC11BS"), the original unscrambled person identifier ("31313"), and all other person identifiable attributes. Using this information, escrow agent 16 either creates a new universal anonymous identifier ("39863211") if the person is new in the system, or looks up the universal anonymous identifier previously assigned to the person. Escrow agent 16 then transmits the mapping from the universal anonymous identifier to the scrambled person identifier to database 20. The data provider identifier may also be sent to database 20. The universal anonymous identifier is substituted for the scrambled person identifier in database 20. Once substituted, all data belonging to a person stored in database 20 are identified by or associated with the same unique universal anonymous identifier.

It may be seen that the linking or mapping from the universal anonymous identifier to the person identifier provides the key to unlock the anonymity of the data stored in database 20. This key relationship is held in confidence by trusted escrow agency 16 and is kept separate from the data itself stored in database 20. Without the key relationship, the data in database 20 cannot be linked to any person.

Returning to FIG. 1, the data in database 20 may be accessed by study teams 22 for analysis, research or other purposes. Database inquiries 24 to database produces non-person identifiable data 26 accessed by study teams 22. If for some reason, members of the study team believes that intervention is required or desirable, then a proposal 28 is made to an independent review board 30. The proposal provides a list of one or more universal anonymous identifiers, a suggested intervention method or intervention instructions, and evidence supporting the need for the intervention. Independent review board 30 evaluates proposal 28 and makes a decision whether the proposed intervention should be made. If intervention is deemed appropriate, independent review board 30 assigns a unique case number to the intervention and transmits the case number with the intervention instructions to a certified intervention agent 34. Independent review board 30 also sends the case number with the universal anonymous identifiers(s) to escrow agency 16. Escrow agency 16, upon receipt of the case number and universal anonymous identifier(s), sends the person identifier(s) and other person identifiable attributes associated with the received universal anonymous identifier(s) to intervention agent 34. Intervention agent 34 now has the person identifier(s) and person identifiable attributes along with the intervention instructions. Intervention agent 34 is then able to contact (42) persons 44 as instructed. The intervention method may be telephone calls, written correspondence, physician contact, or any other suitable means. Intervention agent 34 may be an automated process that receives and executes intervention instruction commands from independent review board to automatically prepare a letter or some form of communication for contacting the person. It may be seen that in this procedure, intervention agent 34 does not have access to any data other than person identifiers and intervention instructions, and study teams 22 do not have access to any data other than the anonymous data records.

It is preferable, in order to achieve and maintain security and integrity of system 10, that all entities operate independently from one another. For example, if the system deals with employee medical insurance claim data, independent review board 30, escrow agency 16, and intervention agent 34 are preferably not related entities of the employer and are able to function independently therefrom. Further, escrow agent 16 is required to safeguard the mapping tables between the universal anonymous identifiers and person identifiers and not release this information to persons or entities without the proper credentials. Additionally, whenever data is electronically transferred via a network, it is preferable that data encryption techniques be used to ensure confidentiality of the data. The data are typically housed in databases such as relational databases, object-oriented databases, relational object-oriented databases and the like.

It is contemplated by the teachings of the present invention to apply system 10 to any data of a sensitive confidential nature, such as medical health records, medical claim records, pharmacy records, clinical records, lab test results, occupational health information, worker's compensation information, personnel information, genetic information, and personal financial data.

Although several embodiments of the present invention and its advantages have been described in detail, it should be understood that mutations, changes, substitutions, transformations, modifications, variations, and alterations can be made therein without departing from the teachings of the present invention, the spirit and scope of the invention being set forth by the appended claims.

What is claimed is:

1. A privacy data escrow system, comprising:
    at least one data provider having a plurality of privacy data records of a plurality of persons, each privacy data record being associated with a unique person identifier of a person, each of the at least one data provider having a unique data provider identifier associated therewith;
    an escrow agent in communication with the at least one data provider and operable to receive and store, from the at least one data provider, the plurality of person identifiers and a plurality of unique scrambled person identifiers each having a one-to-one relationship with one of the plurality of person identifiers, and data provider identifiers associated with each person identifier; and
    a database in communication with the at least one data provider and operable to receive and store, from the at least one data provider, the plurality of privacy data records, the plurality of scrambled person identifiers associated with the privacy data records, and the data provider identifiers, the database further operable to receive and store, from the escrow agent, a unique universal anonymous identifier to replace each scrambled person identifier whereby each privacy data record stored in database is identifiable by a universal anonymous identifier.

2. The system, as set forth in claim 1, wherein the escrow agent comprises a mapping table associating the plurality of person identifiers with the universal anonymous identifiers.

3. The system, as set forth in claim 1, wherein the privacy data record comprises medical insurance claim data.

4. The system, as set forth in claim 1, wherein the privacy data record comprises occupational health data.

5. The system, as set forth in claim 1, wherein the privacy data record comprises worker's compensation data.

6. The system, as set forth in claim 1, wherein the privacy data record comprises electronic medical record, clinical data, pharmacy data and medical data.

7. The system, as set forth in claim 1, wherein the at least one data provider comprises a data scrambler operable to scramble the person identifier and generate the scrambled person identifier.

8. The system, as set forth in claim 1, further comprising an intervention agent in communication with the escrow agent and operable to receive a person identifier therefrom and performing intervention with the person identified by the person identifier.

9. The system, as set forth in claim 1, further comprising:
    a study team operable to access the privacy data record stored in the database and generating proposed interventions;
    an independent review board operable to review and authorize the proposed interventions, the independent review board assigning a case number to an authorized intervention;
    the escrow agent receiving the intervention case number and at least one universal anonymous identifier associated with the authorized intervention; and
    an intervention agent operable to receive the intervention case number and authorized intervention from the independent review board and further receive, from the escrow agent, at least one person identifier associated with the intervention case number.

10. A privacy data escrow system, comprising:
    at least one data provider having a plurality of privacy data records of a plurality of persons, each privacy data record being associated with a unique person identifier of a person, each of the at least one data provider having a unique data provider identifier associated therewith, the at least one data provider being operable to scramble the person identifiers and generate unique scrambled person identifiers therefrom;
    an escrow agent in communication with the at least one data provider and operable to receive and store, from the at least one data provider, the plurality of person identifiers, the associated scrambled person identifiers, and the associated data provider identifier, the escrow agent being operable to generate a unique universal anonymous identifier for each scrambled person identifier;
    a database in communication with the at least one data provider and operable to receive and store, from the at least one data provider, the plurality of privacy data records, the plurality of scrambled person identifiers associated with the privacy data records, and the data provider identifier, the database further operable to receive and store, from the escrow agent, a unique universal anonymous identifier to replace each scrambled person identifier whereby each privacy data record stored in database is identifiable by a universal anonymous identifier.

11. The system, as set forth in claim 10, wherein the escrow agent comprises a mapping table associating the plurality of person identifiers with the universal anonymous identifiers.

12. The system, as set forth in claim 10, further comprising an intervention agent in communication with the escrow agent and operable to receive a person identifier therefrom and performing intervention with the person identified by the person identifier.

13. The system, as set forth in claim 10, further comprising:
    a study team operable to access the privacy data record stored in the database and generating proposed interventions;
    an independent review board operable to review and authorize the proposed interventions, the independent review board assigning a case number to an authorized intervention;
    the escrow agent receiving the intervention case number and at least one universal anonymous identifier associated with the authorized intervention; and
    an intervention agent operable to receive the intervention case number and authorized intervention from the independent review board and further receive, from the escrow agent, at least one person identifier associated with the intervention case number.

14. A method of maintaining the confidentiality of privacy data, comprising:

associating a unique person identifier with each privacy data record;

scrambling the unique person identifier and generating a scrambled person identifier;

transmitting the privacy data record and the scrambled person identifier to a database for storage;

transmitting the person identifier with its associated scrambled person identifier to an escrow agent for confidential safekeeping;

generating, by the escrow agent, a universal anonymous identifier for each person identifier and scrambled person identifier, and transmitting the universal anonymous identifier and its associated scrambled person identifier to the database.

15. The method, as set forth in claim 14, wherein a data provider associates the unique person identifier with each privacy data record and scrambles the person identifier, the data provider further associates a data provider identifier with the privacy data record.

16. The method, as set forth in claim 15, further comprising:

transmitting the data provider identifier with the person identifier and scrambled person identifier to the escrow agent;

transmitting, by the data provider, the data provider identifier with the scrambled person identifier and privacy data record to the database; and transmitting the data provider identifier with the scrambled person identifier and the universal anonymous identifier to the database.

17. The method, as set forth in claim 14, further comprising:

authorizing an intervention in response to studying data in the database;

transmitting a universal anonymous identifier to the escrow agent;

transmitting, by the escrow agency, a person identifier associated with the universal anonymous identifier to an intervention agent; and contacting the person identified by the person identifier.

18. The method, as set forth in claim 14, further comprising:

proposing an intervention having at least one universal anonymous identifier and intervention instructions;

authorizing the intervention and assigning an intervention case number to the intervention;

transmitting a universal anonymous identifier and the intervention case number to the escrow agent;

transmitting, by the escrow agent, a person identifier associated with the universal anonymous identifier and the intervention case number to an intervention agent; and contacting, by the intervention agent, the person identified by the person identifier according to the intervention instructions.

19. The method, as set forth in claim 14, further comprising studying the privacy data record stored in the database by a study team and generating the proposed intervention.

* * * * *